(12) United States Patent
Masui et al.

(10) Patent No.: US 12,019,017 B2
(45) Date of Patent: Jun. 25, 2024

(54) GAS SENSING WITH POROUS SCATTERING MATERIAL

(71) Applicant: Lumileds LLC, San Jose, CA (US)

(72) Inventors: Hisashi Masui, Newark, CA (US); Oleg Borisovich Shchekin, San Francisco, CA (US); Franklin Chiang, Campbell, CA (US)

(73) Assignee: Lumileds LLC, San Jose, CA (US)

( * ) Notice: Subject to any disclaimer, the term of this patent is extended or adjusted under 35 U.S.C. 154(b) by 855 days.

(21) Appl. No.: 17/090,090

(22) Filed: Nov. 5, 2020

(65) Prior Publication Data
US 2021/0247309 A1    Aug. 12, 2021

Related U.S. Application Data

(60) Provisional application No. 63/093,978, filed on Oct. 20, 2020, provisional application No. 62/971,756, filed on Feb. 7, 2020.

(51) Int. Cl.
*G01N 21/47* (2006.01)
*G01N 21/61* (2006.01)
*G01N 33/00* (2006.01)

(52) U.S. Cl.
CPC ............. *G01N 21/61* (2013.01); *G01N 21/47* (2013.01); *G01N 33/0004* (2013.01);
(Continued)

(58) Field of Classification Search
CPC ..................................................... G01N 21/61
(Continued)

(56) References Cited

U.S. PATENT DOCUMENTS

| 10,613,028 B2 | 4/2020 | Lee et al. |
| 2007/0114421 A1 | 5/2007 | Maehlich et al. |

(Continued)

FOREIGN PATENT DOCUMENTS

| CN | 106841038 A | 6/2017 |
| CN | 109870414 | 6/2019 |

(Continued)

OTHER PUBLICATIONS

"International Application Serial No. PCT/US2021/016933, International Search Report dated Jun. 1, 2021", 3 pgs.
(Continued)

*Primary Examiner* — Walter L Lindsay, Jr.
*Assistant Examiner* — Philip T Fadul
(74) *Attorney, Agent, or Firm* — Schwegman, Lundberg & Woessner, P.A.

(57) ABSTRACT

A gas sensing system can allow a gas sample to permeate hollow spaces within a porous scattering material. The porous scattering material can be substantially transparent at an illumination wavelength. An emitter can illuminate the porous scattering material and the gas sample with light having a spectrum that includes the illumination wavelength. A sensor can detect a level of light that has traversed the porous scattering material. Using, for example, the Beer-Lambert Law, the system can determine a concentration of the gas material in the gas sample. The scattering can greatly increase an optical path length through the porous scattering material, compared with a linear dimension of the porous scattering material. The increased optical path length can allow a gas chamber to shrink in size, thereby decreasing a size of the gas sensing system without a corresponding decrease in a sensitivity and/or an accuracy of the system.

17 Claims, 12 Drawing Sheets

(52) U.S. Cl.
CPC ....... *G01N 33/004* (2013.01); *G01N 33/0047* (2013.01); *G01N 2201/0631* (2013.01); *G01N 2201/0636* (2013.01)

(58) Field of Classification Search
USPC ........................................................ 73/31.05
See application file for complete search history.

(56) References Cited

U.S. PATENT DOCUMENTS

| | | | |
|---|---|---|---|
| 2014/0204382 | A1* | 7/2014 | Christensen ......... G01N 21/031 356/402 |
| 2016/0231244 | A1 | 8/2016 | Camargo et al. |
| 2018/0259452 | A1 | 9/2018 | Li et al. |
| 2020/0072740 | A1* | 3/2020 | Venturini .............. G01J 3/0208 |
| 2022/0381658 | A1* | 12/2022 | Boies ................. G01N 15/0618 |

FOREIGN PATENT DOCUMENTS

| | | |
|---|---|---|
| KR | 100494103 B1 | 6/2005 |
| KR | 100732709 B1 | 6/2007 |
| KR | 20100115098 | 10/2010 |
| KR | 101895236 B1 | 9/2018 |
| WO | 2018210583 | 11/2018 |

OTHER PUBLICATIONS

"International Application Serial No. PCT/US2021/016933, Written Opinion dated Jun. 1, 2021", 5 pgs.

"International Application Serial No. PCT US2021 016921, International Search Report dated Jun. 1, 2021", 4 pgs.

"International Application Serial No. PCT US2021 016921, Written Opinion dated Jun. 1, 2021", 5 pgs.

"International Application Serial No. PCT/US2021/016921, International Preliminary Report on Patentability dated Aug. 18, 2022", 7 pgs.

"International Application Serial No. PCT/US2021/016933, International Preliminary Report on Patentability dated Aug. 18, 2022", 7 pgs.

\* cited by examiner

GAS SENSING WITH POROUS SCATTERING MATERIAL

CROSS-REFERENCE TO RELATED APPLICATIONS

This application claims the benefit of priority of U.S. Provisional Application No. 62/971,756, filed Feb. 7, 2020 and entitled, "GAS SENSOR PACKAGING TECHNIQUE USING MWIR EMITTER AND DETECTOR" and U.S. Provisional Application No. 63/093,978, filed Oct. 20, 2020 and entitled, "GAS SENSING SYSTEM HAVING QUADRIC REFLECTIVE SURFACE," both of which are hereby incorporated by reference in their entireties.

TECHNICAL FIELD

The present disclosure relates to detecting a concentration of a gas.

BACKGROUND

There is ongoing effort to improve detecting a concentration of a gas.

Figure 1:
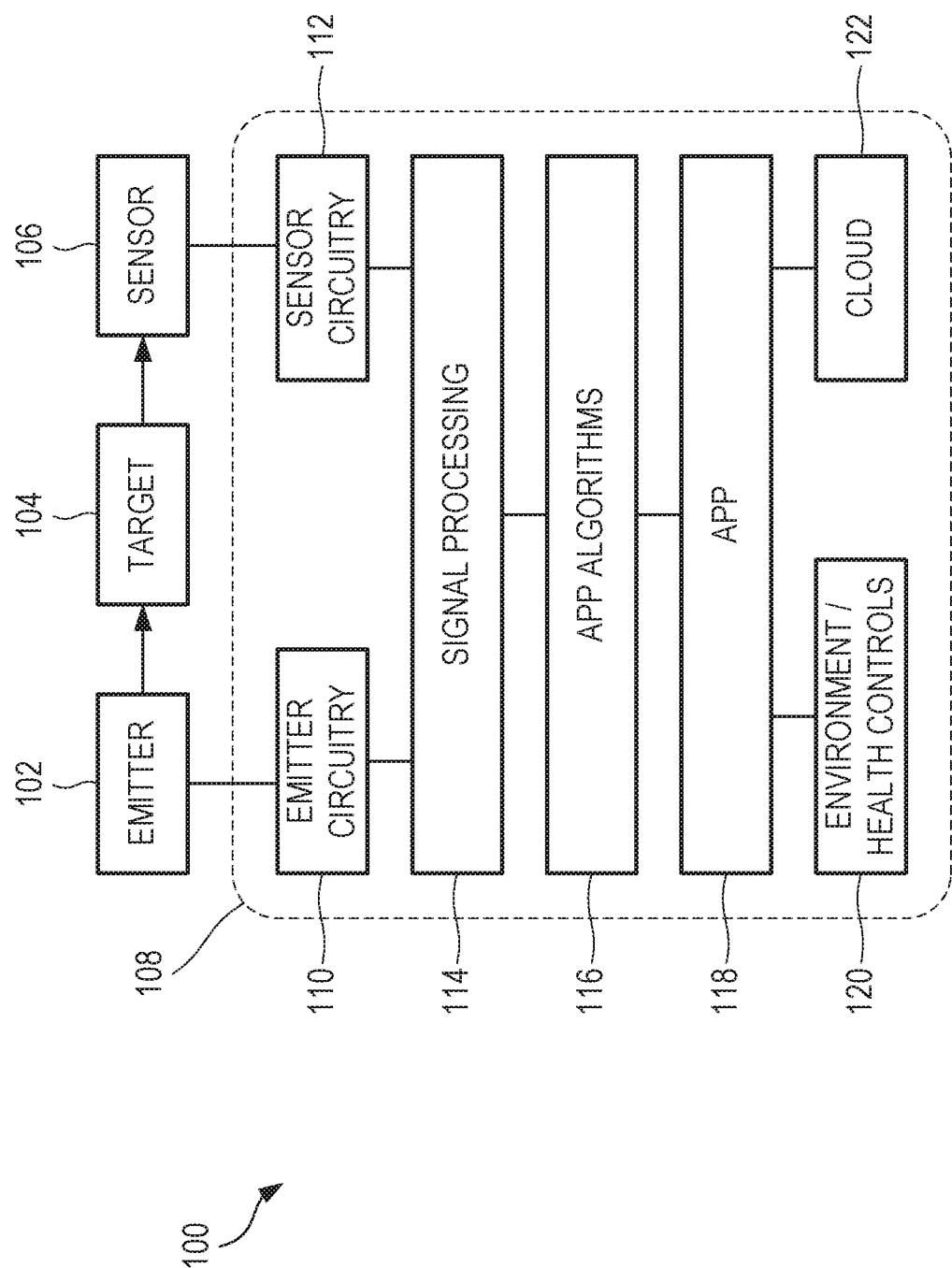
FIG. 1 shows a schematic drawing of an example of a gas sensing system, in accordance with some embodiments.

Corresponding reference characters generally indicate corresponding parts throughout the several views. Elements in the drawings are not necessarily drawn to scale. The configurations shown in the drawings are merely examples and should not be construed as limiting the scope of the disclosed subject matter in any manner.

DETAILED DESCRIPTION

Gas detection is becoming more common for a variety of applications. For example, detecting concentration levels of methane can help guide downstream decisions in the fields of industrial oil and gas exploration, safety, climate change, and others. Detecting concentration levels of formaldehyde and/or volatile organic compounds (VOCs) can help guide downstream decisions in the fields of air quality, safety, and others. Detecting concentration levels of carbon dioxide can help guide downstream decisions in the fields of smart buildings, air quality, capnography, climate change, and others. Detecting concentration levels of carbon monoxide and/or nitrogen dioxide can help guide downstream decisions in the fields of safety and others. Detecting concentration levels of ammonia, sulfur hexafluoride, and/or volatile organic compounds can help guide downstream decisions in the fields of refrigeration, electrical systems, and others. Detecting concentration levels of glucose can help guide downstream decisions in the fields of medicine and others.

Some gas detection systems can make use of a natural absorption of a gas material. For example, methane is found to be absorbent at a wavelength of about 3.3 microns. When a gas sample is illuminated with light at the wavelength of about 3.3 microns, methane in the gas sample can absorb some of the illumination. A sensor or detector in the gas detection system can measure the illumination remaining after the illumination passes through the gas sample.

One category of these illumination/detection gas detection systems can be based on the Beer-Lambert Law. In this category, the gas detection system illuminates the gas with light at or near the absorbent wavelength (or with light having a spectrum that includes the absorbent wavelength) and detects how much of the illuminating light passes through the gas sample. Based on the fraction of illuminating light that emerges from the gas sample, the gas detection system can calculate a concentration level of the particular gas in the gas sample.

For gas detection systems based on the Beer-Lambert Law, the sensitivity and/or accuracy can scale with an optical path length over which the absorption can occur. As a result, gas detection systems with larger gas chambers tend to be more sensitive and/or more accurate than those with smaller gas chambers. For example, in a gas detection system in which the gas chamber is hollow, the illumination can progress in a straight line through the gas chamber, such that the optical path length can be comparable to a dimension of the gas chamber.

There is marketplace pressure to shrink the gas detection systems, so that they may be included with more consumer goods, such as in a heating, ventilation, and air conditioning (HVAC) system, a smart speaker, in an automobile (such as in a fuel system, an in-cabin ventilation system, and/or an exhaust system), a refrigeration system, and others. However, shrinking the gas detection systems to fit into smaller spaces can compromise the sensitivity and/or accuracy of the system.

To improve the sensitivity and/or accuracy of the system, various embodiments of the gas detection systems described herein dispose a porous scattering material in the gas chamber and/or in a wall surrounding the gas chamber, so that a gas sample can permeate hollow spaces within the porous scattering material. The scattering material can be transparent at about the illuminating wavelength (e.g., the wavelength at which the gas material is absorbent).

The scattering material can greatly increase an optical path length of illuminating light that passes through the scattering material, compared with a single pass through a given volume (e.g., a linear dimension of the porous scattering material, or a path that would be taken if the space occupied by the porous scattering material were instead hollow). For example, in various embodiments of the gas detection system described herein, the scattering material can redirect the illumination multiple times within the scattering material. The actual optical path traversed by the illumination in the scattering material can be orders of magnitude larger than the actual size of the scattering material. As a result, the optical path length experienced by the illumination can be significantly greater than a dimension of the gas chamber, such by a factor of 10, 100, or more.

As a result of locating the porous scattering material inside the gas chamber and/or in a wall of the gas chamber, the gas chamber size can be decreased significantly, in order to maintain a sensitivity/accuracy comparable to what would be achieved by a system having a hollow gas chamber. Consequently, the gas detection systems described herein, which can dispose a porous scattering material in the gas chamber and/or in a wall of the gas chamber, can be significantly smaller than comparable systems that have a hollow gas chamber (optionally with impermeable walls), while achieving sensitivity/accuracy performance comparable to systems that have a hollow gas chamber (optionally with impermeable walls).

A gas sensing system can allow a gas sample to permeate hollow spaces within a porous scattering material. The porous scattering material can be substantially transparent at an illumination wavelength. An emitter can illuminate the porous scattering material and the gas sample with light having a spectrum that includes the illumination wavelength. A sensor can detect a level of light that has traversed the porous scattering material. Using the Beer-Lambert Law, the system can determine a concentration of the gas material in the gas sample. The scattering can greatly increase an optical path length through the porous scattering material, compared with a linear dimension of the porous scattering material (e.g., a path that would be taken if the space occupied by the porous scattering material were instead hollow). The increased optical path length can allow a gas chamber to shrink in size, thereby decreasing a size of the gas sensing system without a corresponding decrease in a sensitivity and/or an accuracy of the system.

FIG. 1 shows a schematic drawing of an example of a gas sensing system 100, in accordance with some embodiments.

As shown in the example of FIG. 1, an emitter 102 can emit light toward a target 104. The target 104 can include a porous scattering material, such as disposed in a gas chamber and/or in one or more walls of a gas chamber, so that a gas sample can permeate hollow spaces within the porous scattering material, such as inside the gas chamber. A sensor 106 can detect light, emitted from the emitter 102, that has traversed through the target 104. At least one processor 108, coupled to the sensor 106, can determine a concentration of a specified gas material in the gas sample.

The emitter 102 can be selected to emit light that can include a wavelength that is relatively strongly absorbed by the gas material that is to be detected.

For example, methane has an absorption peak (e.g., a wavelength at which absorption is relatively large, compared to the absorption at adjacent wavelengths) at a wavelength of about 3.3 microns. To detect a concentration of methane in the gas sample, the emitter 102 can emit light at about 3.3 microns. Similarly, the emitter 102 can emit light at about 3.6 microns to detect formaldehyde and/or volatile organic compounds. The emitter 102 can emit light at about 4.3 microns to detect carbon dioxide. The emitter 102 can emit light at about 4.5 microns to detect carbon monoxide. The emitter 102 can emit light at about 4.7 microns to detect nitrogen dioxide. The emitter 102 can emit light at about 9 microns to detect ammonia, sulfur hexafluoride, and/or certain volatile organic compounds. The emitter 102 can emit light at about 10.4 microns to detect glucose. These numerical examples are but examples. Other suitable wavelengths can also be used to detect other gas materials or compounds.

The emitter 102 can emit light having a spectrum that is relatively sharply peaked. The emitter 102 can emit light having a spectrum that is relatively broad. The emitter 102 can emit light having a spectrum that includes the wavelength at which absorption of the gas material or compound is relatively high. The emitter 102 can emit light in the infrared portion, the visible portion, and/or the ultraviolet portion of the electromagnetic spectrum. The emitter 102 can emit light in the Medium Wavelength Infrared (MWIR) portion of the electromagnetic spectrum, with a wavelength range extending from about 3 microns to about 5 microns. The emitter 102 can emit light in the Long Wavelength Infrared (LWIR) portion of the electromagnetic spectrum, with a wavelength range extending from about 8 microns to about 14 microns.

In various embodiments, the emitter 102 can include one or more light-emitting diodes (LEDs). The one or more light-emitting diodes can include III-V semiconductor materials (or other semiconductor materials from, for example, group II-VI). The one or more light-emitting diodes can include GaSb, InP, InAs, or other suitable materials. The emitter 102 can include one or more lasers. The emitter 102 can include one or more broadband sources that are spectrally filtered.

The target 104 can include a porous scattering material, such as porous alumina, porous silicon, porous YAG, porous $TiO_2$, and others. The porous scattering material can be disposed in a gas chamber and/or in a wall or walls of the gas chamber, so that a gas sample can permeate hollow spaces within the porous scattering material inside the gas chamber and/or in the wall or walls of the gas chamber. The porous scattering material can be transparent, or substantially transparent, at the wavelength of the light emitted by the emitter 102. The porous scattering material can be transparent, or substantially transparent, at the wavelength at which the gas material is relatively absorbent. The target 104 and the porous scattering material can be sized and shaped in any suitable manner; examples follow below in FIGS. 3-8.

The sensor 106 can detect light, emitted from the emitter 102, that has traversed through the target 104. The sensor 106 can include one or more pixels (e.g., detector elements or sensor elements) or other types of sensors known in the art. In some embodiments, the sensor 106 can be separate from the emitter 102. The sensor 106 can include one or more sensor elements that are formed from a same or similar semiconductor material that is used in the emitter 102.

The sensor 106 can optionally be formed integrally with the emitter 102. For example, the sensor 106 and the emitter 102 can both be formed as light-emitting diodes in a single array or in a single integral package. The emitter 102 can be forward biased. The sensor 106 can be reverse biased. Other configurations can also be used.

The at least one processor 108, coupled to the sensor 106, can determine a concentration of a specified gas material in the gas sample.

The at least one processor 108 can include emitter circuitry 110 that can drive the emitter 102.

The at least one processor 108 can include sensor circuitry 112 that can determine a power level of light that strikes the sensor 106. The sensor circuitry 112 can optionally include an analog-to-digital converter.

The at least one processor 108 can include signal processing circuitry 114 that can analyze an output of the sensor circuitry 112. For example, the signal processing circuitry 114 can receive a value that represents a sensed optical power value, and can calculate, from the received value, a concentration level of the gas material in the gas sample. The signal processing circuitry 114 can employ the Beer-Lambert Law to perform the calculation, although other suitable calculations can be performed.

The at least one processor 108 can include one or more application algorithms 116 that can serve as an interface between the signal processing circuitry 114 and an application that includes a user interface.

The at least one processor 108 can include one or more applications 118 that can interface with the one or more application algorithms 116. The one or more application algorithms 116 can communicate with one or more servers dedicated to the environment and/or health controls 120. The one or more application algorithms 116 can communicate with one or more servers connected to the cloud 122.

The gas sensing system 100 can optionally detect two or more gas materials in a same gas sample. The two or more gas materials can have different wavelengths at which the respective gas materials are relatively absorbent. The emitter 102 can emit light at respective two or more wavelengths. The sensor 106 can sense light at the two or more wavelengths. To sense at the wavelengths, the gas sensing system 100 can include one or more wavelength-sensitive filters, such as to direct one wavelength onto one sensor element and direct another wavelength onto another sensor element.

In some examples, the emitter 102 can optionally emit reference light having a spectrum that includes a reference wavelength different from the detection wavelength. The gas sample can interact with the light at the detection wavelength, but may not interact with the reference light at the reference wavelength. The sensor 106 can optionally detect at least some of the reference light. The at least one processor 108 can use the level of the reference light at the sensor 106, in addition to the level of the detection light at the sensor 106, to determine the concentration of the gas material in the gas sample. In some examples, for which the gas sensing system 100 can sense two different gas materials, the emitter can emit a first wavelength and a second wavelength. The wavelengths can be selected such that a first gas interacts with the first wavelength but not the second wavelength and a second gas interacts with the second wavelength but not the first wavelength. Light at the second wavelength can serve as a reference for detecting the first gas, while light at the first wavelength can serve as a reference for detecting the second gas. Other combinations can also be used.

Figure 2:
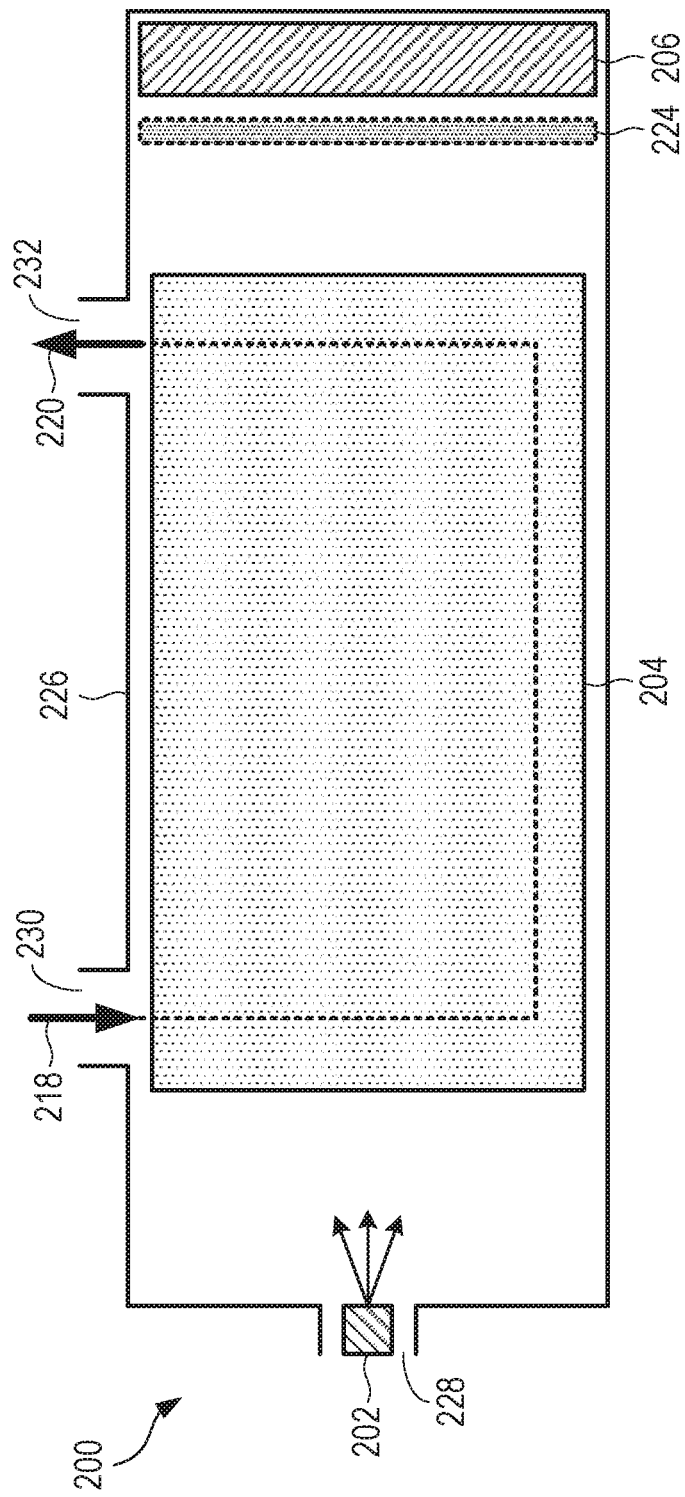
FIG. 2 shows a cross-sectional side view of an example of a gas sensing system, in accordance with some embodiments.

FIG. 2 shows a cross-sectional side view of an example of a gas sensing system 200, in accordance with some embodiments. FIG. 2 omits the circuitry and plumbing of the gas sensing system 200; any suitable circuitry and plumbing can also be used as will be recognized by a person of ordinary skill in the art upon reading and understanding the disclosed subject matter.

An emitter 202, positioned in, at, or near an illumination port 228 of a gas chamber 226, can emit light toward a target 204. The target 204 can include a porous scattering material disposed in the gas chamber 226, so that a gas sample can permeate hollow spaces within the porous scattering material inside the gas chamber 226. A sensor 206 can detect light, emitted from the emitter 202, that has traversed through the target 204. The emitter 202 can be the same as or similar to the emitter 102 of FIG. 1. Further, the sensor 206 may be the same as or similar to the sensor 106 of FIG. 1.

An optional wavelength filter 224 can filter out light having wavelengths away from the emitted wavelength and/or the wavelength at which the gas material is absorbent. For example, the wavelength filter 224 can block at least one spectral portion of scattered light having wavelengths away from the first wavelength. The optional wavelength filter 224 can improve a signal-to-noise ratio of the gas sensing system 200.

The gas sensing system 200 can optionally include plumbing to move the gas sample into and/or out of the target 204. The gas sensing system 200 can include an intake 218 through an intake port 230 of the gas chamber 226. The gas sensing system 200 can include an outlet 220 through an outlet port 232 of the gas chamber 226.

In the example of FIG. 2, the target 204 can be located between the emitter 202 and the sensor 206. In the example of FIG. 2, the target 204 can be elongated along an axis that extends between a center of the emitter 202 and a center of the sensor 206. The geometry of FIG. 2 is but one example of a geometry for a gas sensing system 200; other geometries are also possible.

Figure 3:
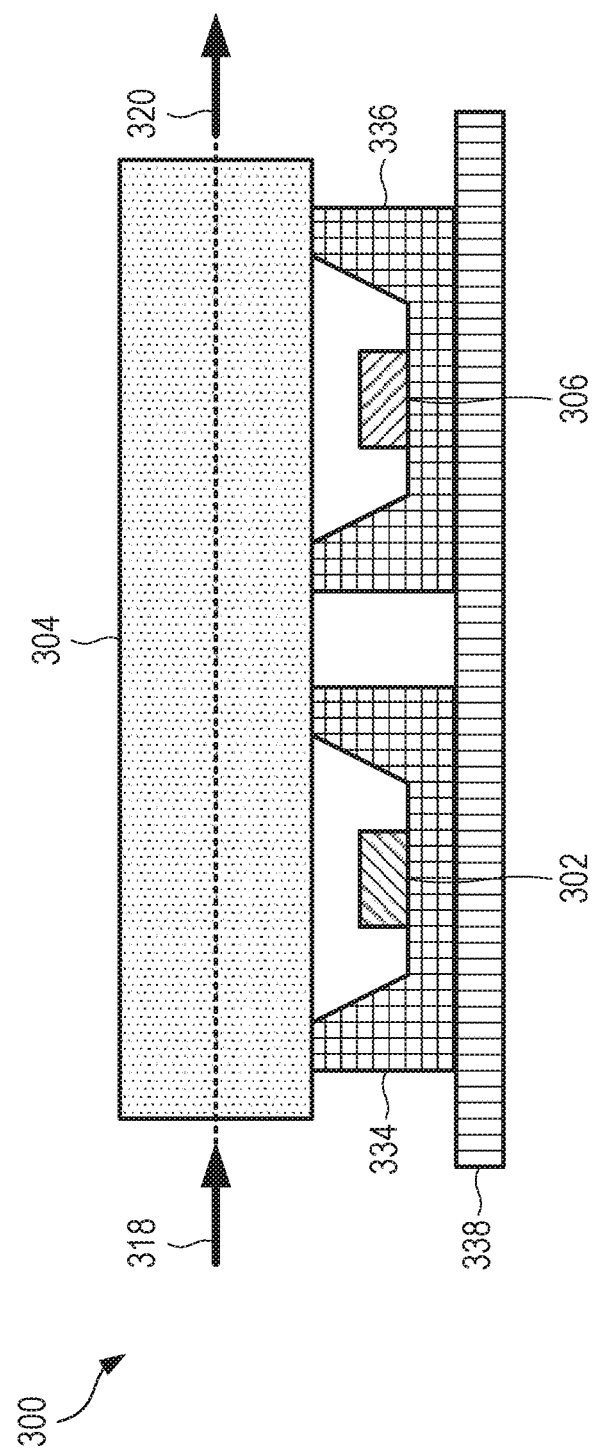
FIG. 3 shows a cross-sectional side view of an example of a gas sensing system, in accordance with some embodiments.

FIG. 3 shows a cross-sectional side view of an example of a gas sensing system 300, in accordance with some embodiments. FIG. 3 omits the circuitry of the gas sensing system 300; any suitable circuitry can also be used as described above with reference to FIG. 2.

An emitter 302 can emit light toward a target 304. The target 304 can include a porous scattering material, so that a gas sample can permeate hollow spaces within the porous scattering material. A sensor 306 can detect light, emitted from the emitter 302, that has traversed through the target 304. The emitter 302 can be the same as or similar to the emitter 102 of FIG. 1. Further, the sensor 306 may be the same as or similar to the sensor 106 of FIG. 1.

In the target 304 of FIG. 3, and in the targets shown in FIGS. 1 and 2, and as described below with reference to FIGS. 4-8, the scattering effect of the porous scattering material can cause the light emerging from the target 304 to emerge isotropically or substantially isotropically (e.g., with uniform or nearly uniform power emission in all directions) from the target 304. As a result, the sensor 306 need not be positioned linearly with respect to the emitter 302 and the target 304. For example, the emitter 302 and the sensor 306 can be on a same side of the target 304.

The emitter 302 can be positioned in a package 334 that can be reflective. The package 334 can reflect at least portions of any incident light toward the target 304. In some examples, the package 334 can be an emitter reflective package that defines a volume that is bounded by the target 304 and a reflective inner surface of the emitter reflective package. Such a package 334 can increase the fraction of light emitted from the emitter 302 that enters the target 304.

Similarly, the sensor 306 can be positioned in a package 336 that can be reflective. The package 336 can reflect at least portions of any incident light toward the sensor 306. In some examples, the package 336 can be a sensor reflective package that defines a volume that is bounded by the target 304 and a reflective inner surface of the sensor reflective package. Such a package 336 can increase the amount of light from the target 304 that strikes the sensor 306.

A tile 338, such as a ceramic tile, can mechanically support the package 334 and the package 336, which in turn can mechanically support the target 304.

The gas sensing system 300, as well as any or all of the other configurations shown and described herein, can optionally include plumbing to move the gas sample into and/or out of the target 304. The gas sensing system 300 can include an intake 318 and an outlet 320.

In the example of FIG. 3, the target 304 can be elongated along an elongation axis, and the emitter 302 and the sensor 306 are located on a same side of a plane that includes the elongation axis. The geometry of FIG. 3 is but one example of a geometry for a gas sensing system 300; other geometries are also possible.

Figure 4:
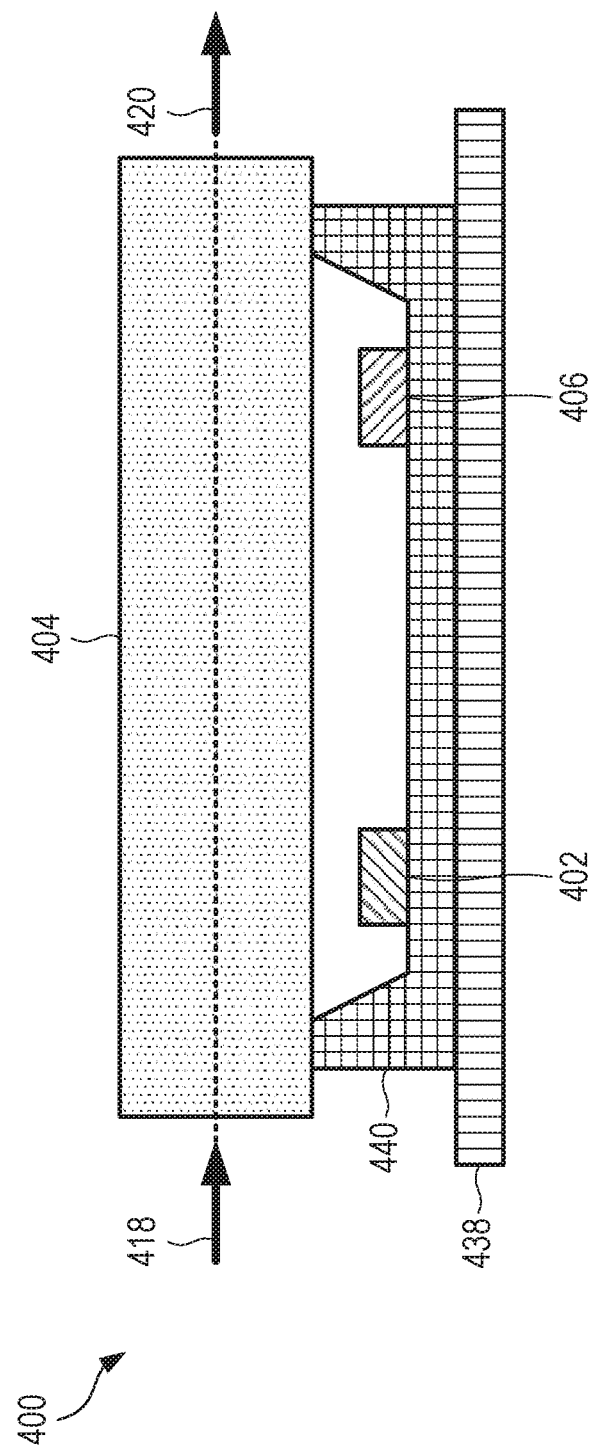
FIG. 4 shows a cross-sectional side view of an example of a gas sensing system, in accordance with some embodiments.

FIG. 4 shows a cross-sectional side view of an example of a gas sensing system 400, in accordance with some embodiments. FIG. 4 omits the circuitry of the gas sensing system 400; any suitable circuitry can also be used as will be recognized by a person of ordinary skill in the art upon reading and understanding the disclosed subject matter.

An emitter 402 can emit light toward a target 404. The target 404 can include a porous scattering material, so that a gas sample can permeate hollow spaces within the porous scattering material. A sensor 406 can detect light, emitted from the emitter 402, that has traversed through the target 404. The emitter 402 can be the same as or similar to the emitter 102 of FIG. 1. Further, the sensor 406 may be the same as or similar to the sensor 106 of FIG. 1.

The emitter 402 and the sensor 406 can both be packaged in a single package 440 that can be reflective. In some examples, the package 440 can be a reflective package that defines a volume that is bounded by the target 404 and a reflective inner surface of the reflective package. The package 440 can reflect at least portions of any incident light toward the target 404 or toward the sensor 406.

A tile 438, such as a ceramic tile, can mechanically support the package 440, which in turn can mechanically support the target 404.

The gas sensing system 400, as well as any or all of the other configurations shown and described herein, can optionally include plumbing to move the gas sample into and/or out of the target 404. The gas sensing system 400 can include an intake 418 and an outlet 420.

In the example of FIG. 4, the target 404 can be elongated along an elongation axis, and the emitter 402 and the sensor 406 are located on a same side of a plane that includes the elongation axis. The geometry of FIG. 4 is but one example of a geometry for a gas sensing system 400; other geometries are also possible.

Figure 5:
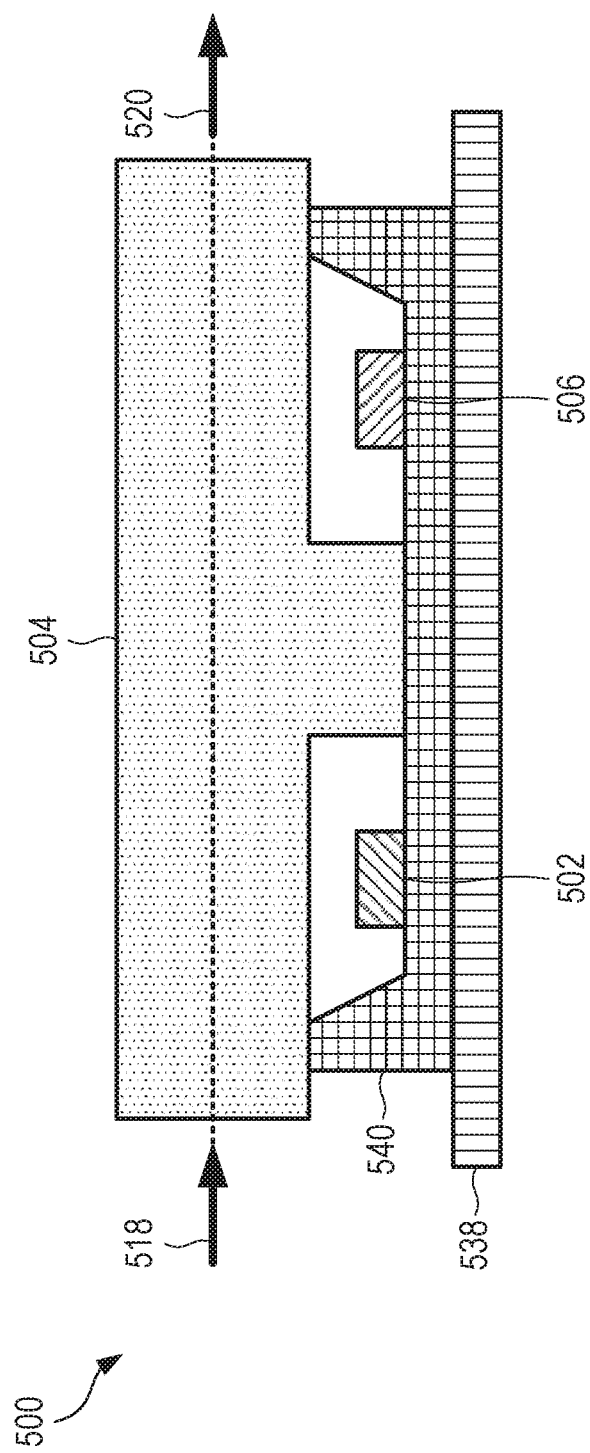
FIG. 5 shows a cross-sectional side view of an example of a gas sensing system, in accordance with some embodiments.

FIG. 5 shows a cross-sectional side view of an example of a gas sensing system 500, in accordance with some embodiments. FIG. 5 omits the circuitry of the gas sensing system 500; any suitable circuitry can also be used as will be recognized by a person of ordinary skill in the art upon reading and understanding the disclosed subject matter.

An emitter 502 can emit light toward a target 504. The target 504 can include a porous scattering material, so that a gas sample can permeate hollow spaces within the porous scattering material. A sensor 506 can detect light, emitted from the emitter 502, that has traversed through the target 504. The emitter 502 can be the same as or similar to the emitter 102 of FIG. 1. Further, the sensor 506 may be the same as or similar to the sensor 106 of FIG. 1.

The emitter 502 and the sensor 506 can both be packaged in a single package 540 that can be reflective. The package 540 can reflect at least portions of any incident light toward the target 504 or toward the sensor 506.

A tile 538, such as a ceramic tile, can mechanically support the package 540, which in turn can mechanically support the target 504.

The target 504 can optionally be shaped to extend toward the package 540. The target 504 can optionally be shaped to contact the package 540.

The gas sensing system 500, as well as any or all of the other configurations shown and described herein, can optionally include plumbing to move the gas sample into and/or out of the target 504. The gas sensing system 500 can include an intake 518 and an outlet 520.

In the example of FIG. 5, the target 504 can be elongated along an elongation axis, and the emitter 502 and the sensor 506 are located on a same side of a plane that includes the elongation axis. The geometry of FIG. 5 is but one example of a geometry for a gas sensing system 500; other geometries are also possible.

Figure 6:
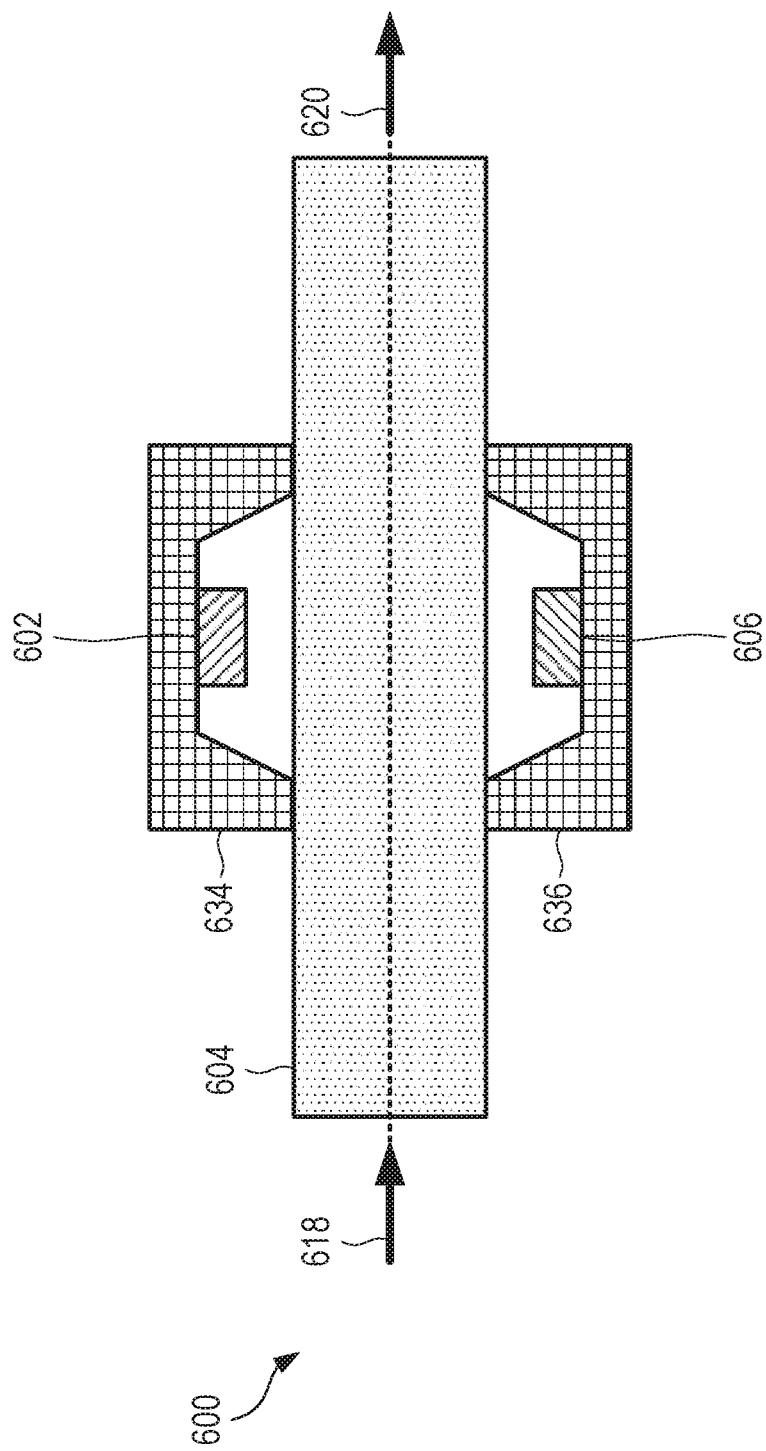
FIG. 6 shows a cross-sectional side view of an example of a gas sensing system, in accordance with some embodiments.

FIG. 6 shows a cross-sectional side view of an example of a gas sensing system 600, in accordance with some embodiments. FIG. 6 omits the circuitry of the gas sensing system 600; any suitable circuitry can also be used as will be recognized by a person of ordinary skill in the art upon reading and understanding the disclosed subject matter.

An emitter 602 can emit light toward a target 604. The target 604 can include a porous scattering material, so that a gas sample can permeate hollow spaces within the porous scattering material. A sensor 606 can detect light, emitted from the emitter 602, that has traversed through the target 604. The emitter 602 can be the same as or similar to the emitter 102 of FIG. 1. Further, the sensor 606 may be the same as or similar to the sensor 106 of FIG. 1.

The emitter 602 can be positioned in a package 634 that can be reflective. The package 634 can reflect at least portions of any incident light toward the target 604. Such a package 634 can increase the fraction of light emitted from the emitter 602 that enters the target 604.

Similarly, the sensor 606 can be positioned in a package 636 that can be reflective. The package 636 can reflect at least portions of any incident light toward the sensor 606. Such a package 636 can increase the amount of light from the target 604 that strikes the sensor 606.

The emitter 602 and the package 634 can be disposed on a first side of a target 604. The sensor 606 and the package 636 can be disposed on a second side of a target 604, opposite the first side. Other positions are also possible.

The gas sensing system 600, as well as any or all of the other configurations shown and described herein, can optionally include plumbing to move the gas sample into and/or out of the target 604. The gas sensing system 600 can include an intake 618 and an outlet 620.

In the example of FIG. 6, the target 604 can be elongated along a first axis that is substantially orthogonal to a second axis that extends between a center of the emitter 602 and a center of the sensor 606. The geometry of FIG. 6 is but one example of a geometry for a gas sensing system 600; other geometries are also possible.

Figure 7:
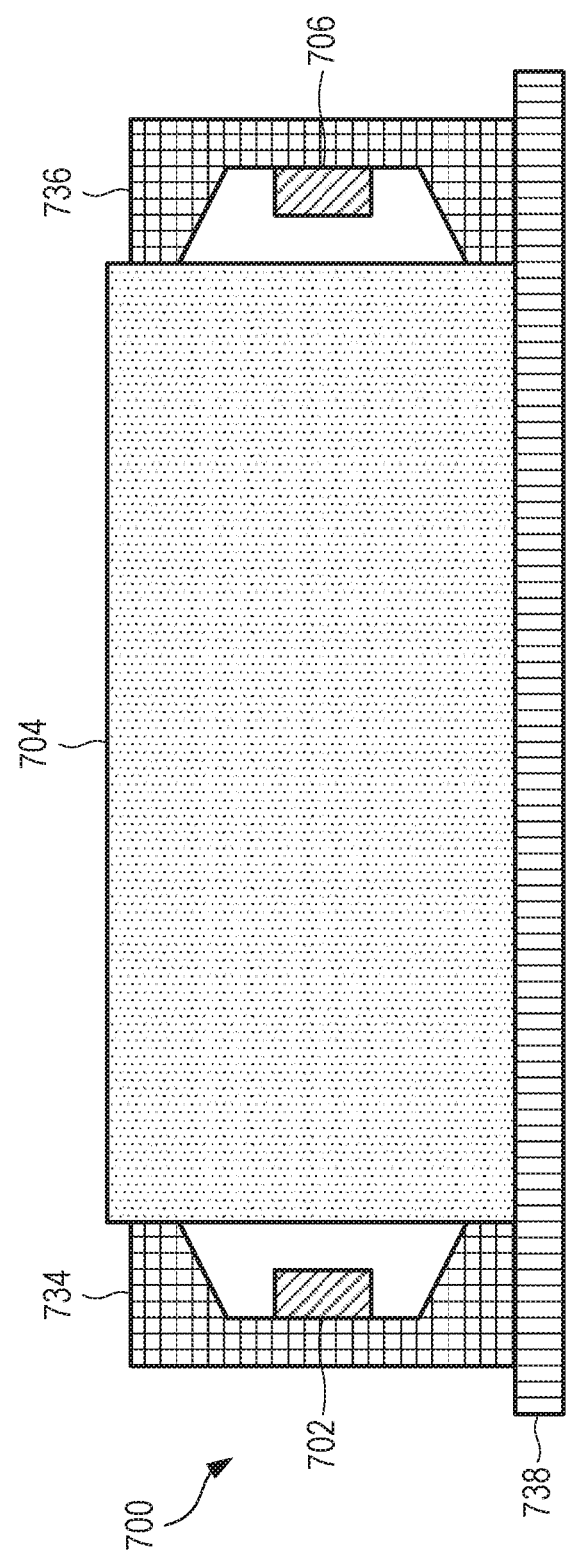
FIG. 7 shows a cross-sectional side view of an example of a gas sensing system, in accordance with some embodiments.

FIG. 7 shows a cross-sectional side view of an example of a gas sensing system 700, in accordance with some embodiments. FIG. 7 omits the circuitry of the gas sensing system 700; any suitable circuitry can also be used as will be recognized by a person of ordinary skill in the art upon reading and understanding the disclosed subject matter.

An emitter 702 can emit light toward a target 704. The target 704 can include a porous scattering material, so that a gas sample can permeate hollow spaces within the porous scattering material. A sensor 706 can detect light, emitted from the emitter 702, that has traversed through the target 704. The emitter 702 can be the same as or similar to the emitter 102 of FIG. 1. Further, the sensor 706 may be the same as or similar to the sensor 106 of FIG. 1.

The emitter 702 can be positioned in a package 734 that can be reflective. The package 734 can reflect at least portions of any incident light toward the target 704. Such a package 734 can increase the fraction of light emitted from the emitter 702 that enters the target 704.

Similarly, the sensor 706 can be positioned in a package 736 that can be reflective. The package 736 can reflect at least portions of any incident light toward the sensor 706. Such a package 736 can increase the amount of light from the target 704 that strikes the sensor 706.

The emitter 702 and the package 734 can be disposed on a first side of a target 704. The sensor 706 and the package 736 can be disposed on a second side of a target 704, opposite the first side. Other positions are also possible.

A tile 738, such as a ceramic tile, can mechanically support one of more of the package 734, the target 704, or the package 736.

The configuration of FIG. 7 can optionally include plumbing (not shown) that can direct a flow, for example, of the gas sample into and/or out of the plane of the page in FIG. 7.

In the example of FIG. 7, the target 704 can be located between the emitter 702 and the sensor 706. In the example of FIG. 7, the target 704 can be elongated along an axis that extends between a center of the emitter 702 and a center of the sensor 706. The geometry of FIG. 7 is but one example of a geometry for a gas sensing system 700; other geometries are also possible.

Figure 8:
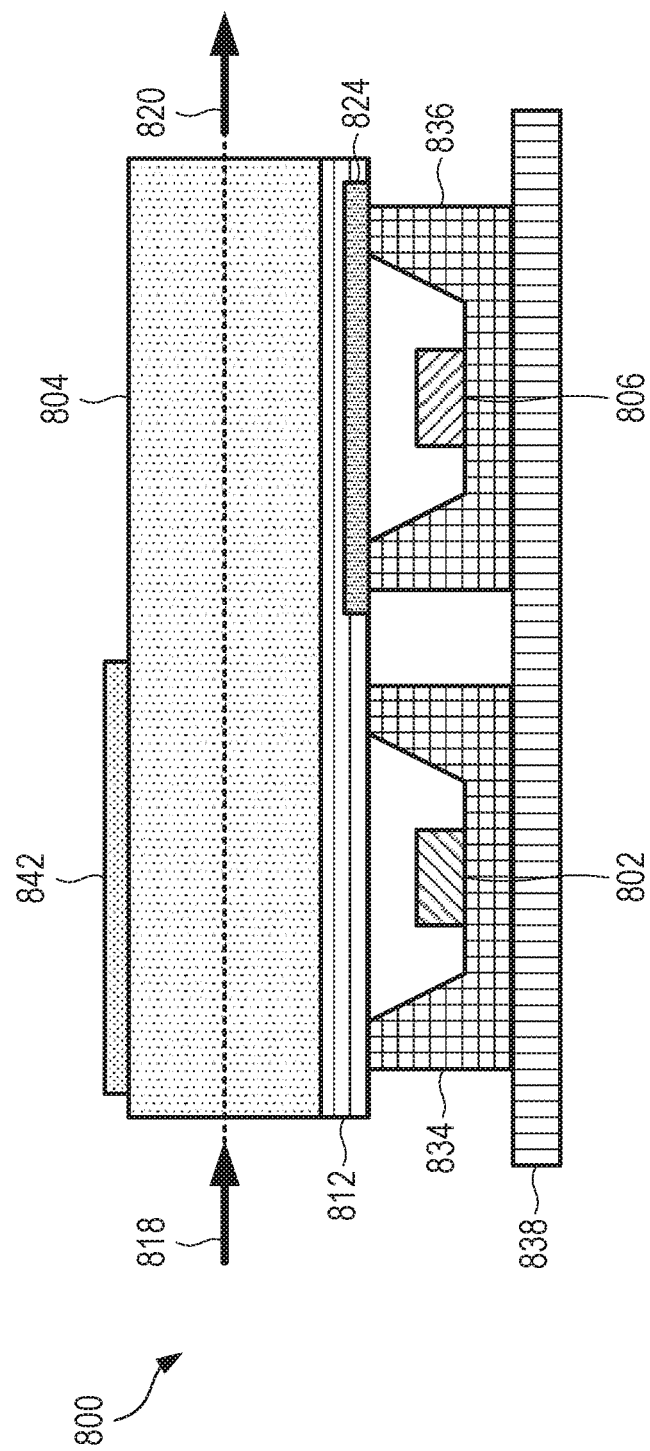
FIG. 8 shows a cross-sectional side view of an example of a gas sensing system, in accordance with some embodiments.

FIG. 8 shows a cross-sectional side view of an example of a gas sensing system 800, in accordance with some embodiments. FIG. 8 omits the circuitry of the gas sensing system 800; any suitable circuitry can also be used as will be recognized by a person of ordinary skill in the art upon reading and understanding the disclosed subject matter.

An emitter 802 can emit light toward a target 804. The target 804 can include a porous scattering material, so that a gas sample can permeate hollow spaces within the porous scattering material. A sensor 806 can detect light, emitted from the emitter 802, that has traversed through the target 804. The emitter 802 can be the same as or similar to the emitter 102 of FIG. 1. Further, the sensor 806 may be the same as or similar to the sensor 106 of FIG. 1.

The emitter 802 can be positioned in a package 834 that can be reflective. The package 834 can reflect at least portions of any incident light toward the target 804. Such a package 834 can increase the fraction of light emitted from the emitter 802 that enters the target 804.

Similarly, the sensor 806 can be positioned in a package 836 that can be reflective. The package 836 can reflect at least portions of any incident light toward the sensor 806. Such a package 836 can increase the amount of light from the target 804 that strikes the sensor 806.

An optional window 812 can be located between the emitter 802 and the target 804, and/or between the target 804 and the sensor 806. The window 812 can optionally include one or more optical filters 824, such as a bandpass filter that blocks light outside a specified range of wavelengths. The one or more filters 824 can be embedded in the window 812. In the embedded environment, the one or more filters 824 can be fabricated in a more precise and flexible environment than if such filters 824 were fabricated separately and/or placed separately. For example, the window 812 can include multiple filters 824 at various locations on and/or in the window 812. The window 812 can be flat (e.g., generally planar) or curved. The window 812 can be smooth or can have a rough surface finish. Further, the optional window 812 with optional one or more filters 824 can optionally be incorporated into any of the other configurations presented herein, including the configurations of FIGS. 3-7.

A tile 838, such as a ceramic tile, can mechanically support one of more of the package 834, or the package 836.

An optional reflector 842 can be located at or near a surface of the target 804. The reflector 842 can reflect back into the target 804 light that would otherwise exit the target and miss the sensor 806. For example, the reflector 842 can receive third light that has exited the target 804 and reflect the third light to reenter the target 804. The reflector 842 can be formed from a metal or other suitable material that is at least partially reflective at a wavelength of light emitted by the emitter 802. Using such a reflector 842 can lengthen a mean optical path length for light that propagates from the emitter 802, through at least a portion of the target 804, to the sensor 806.

The configuration of FIG. 8 can optionally include plumbing (not shown) that can direct a flow of the gas sample into and/or out of the plane of the page in FIG. 8. For example, the gas sensing system 800 can optionally or in addition to can include an intake 818 and an outlet 820.

In the example of FIG. 8, the target 804 can be elongated along an elongation axis, and the emitter 802 and the sensor 806 are located on a same side of a plane that includes the elongation axis. The geometry of FIG. 8 is but one example of a geometry for a gas sensing system 800; other geometries are also possible.

Figure 9:
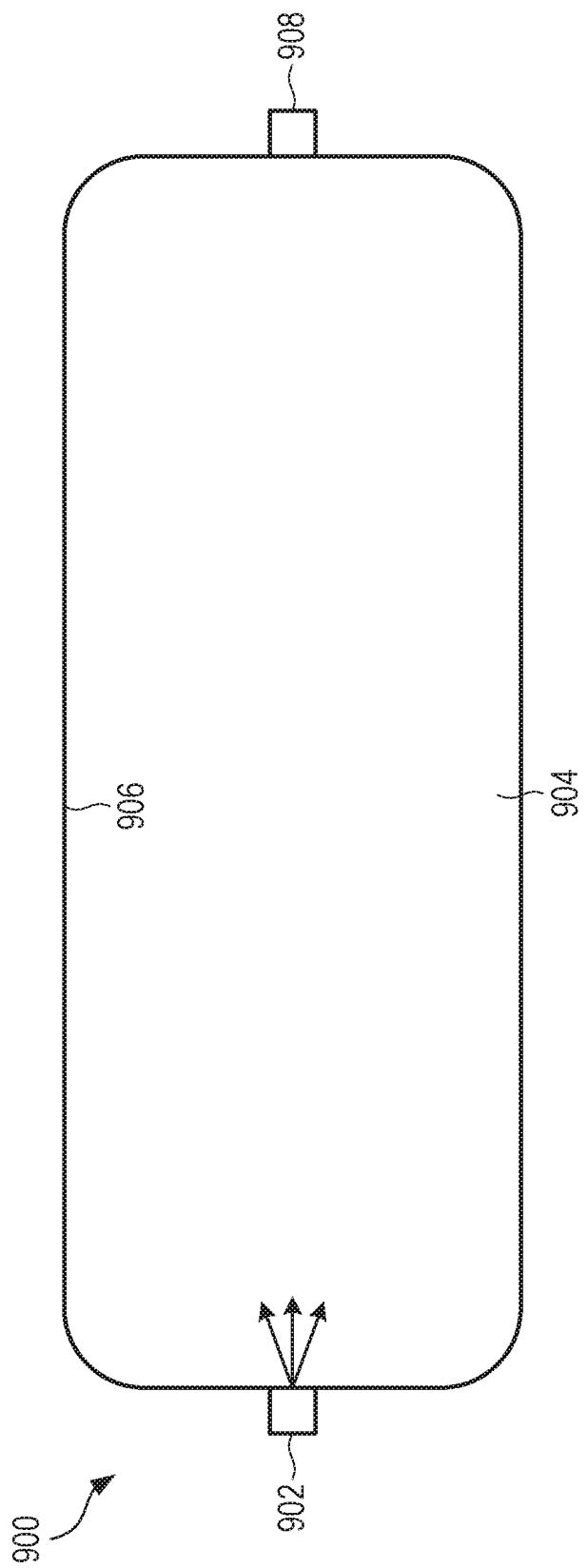
FIG. 9 shows a cross-sectional side view of an example of a gas sensing system, in accordance with some embodiments.

FIG. 9 shows a cross-sectional side view of an example of a gas sensing system 900, in accordance with some embodiments. FIG. 9, as well as FIG. 12 below, omits the circuitry of the gas sensing system 900; any suitable circuitry can also be used as will be recognized by a person of ordinary skill in the art upon reading and understanding the disclosed subject matter. Similarly, FIG. 9, as well as FIG. 12 below, omits plumbing of the gas chamber, which can controllably pump a gas sample into the gas chamber and can controllably pump the gas sample out of the gas chamber, after a measurement has been taken.

The system 900 can include a light emitter 902 that emits light into a gas chamber 904 that is fillable with a gas sample. The gas chamber 904 includes a reflective surface 906, which can form a wall of the gas chamber 904, can be internal to the gas chamber 904, or can be external to the gas chamber 904. A light sensor 908 can receive light from the interior of the gas chamber 904, and can produce an electrical signal that corresponds to an amount of light received by the light sensor 908. One or more processors can receive the electrical signal from the light sensor 908, can use the Beer-Lambert law and the electrical signal level to determine a concentration level of the gas sample, and can output, display, and/or store the determined concentration level.

The reflective surface 906 can optionally be smooth over its full extent and support specular reflection at every location or nearly every location on the reflective surface 906.

The reflective surface 906 can optionally include one or more regions that support diffuse reflection (e.g., reflect with scattering, such that light with a single incident direction can reflect with a multiple exiting directions or a range of exiting directions).

Figure 10:
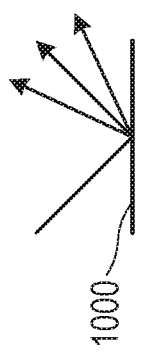
FIG. 10 shows an example of a light ray striking a diffusing portion of a surface, in accordance with some embodiments.

FIG. 10 shows an example of a light ray striking a diffusing portion of a surface 1000, in accordance with some embodiments. The diffusing portion of the surface can diffusely reflect the light ray into multiple light rays having multiple propagation directions. To accomplish the diffuse reflection, the diffusing portion can be roughened, such as roughened at the scale of middle wavelength infrared (MWIR) wavelengths, which would generate a randomized reflection from such a roughened surface for light in the range of MWIR wavelengths. In some examples, the diffusing portion can be formed by disposing a reflecting layer, such as aluminum, on frosted glass. Other manufacturing techniques can also be used.

Figure 11:
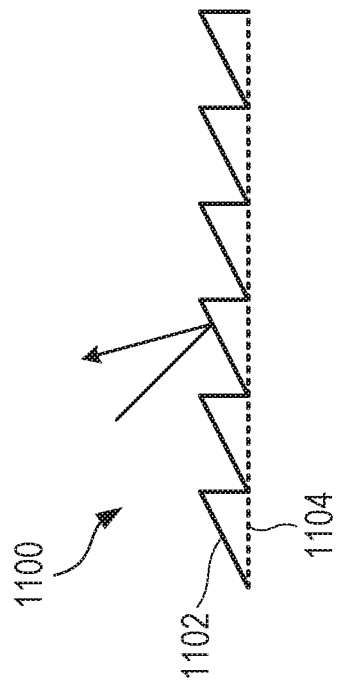
FIG. 11 shows an example of how a light ray striking a portion of a surface can steer a reflection, in accordance with some embodiments.

Returning to FIG. 9, the reflective surface 906 can optionally include one or more regions that are configured to steer reflected light. FIG. 11 shows an example of a light ray striking a portion of a surface 1100 that can steer the reflection, in accordance with some embodiments. For example, the one or more regions can have one or more inclined facets 1102, which can direct incident light into a specified direction other than what can be achieved by reflecting from a baseline surface 1104 that would lack the facets 1102. Other light-steering configurations can also be used.

Returning to FIG. 9, the reflective surface 906 can optionally be impermeable to the gas sample.

The reflective surface 906 can optionally be permeable to the gas sample, such that some of the gas sample can be disposed within the structure that forms the reflective surface 906. As such, the structure that forms the reflective surface 906 can be considered to be a volumetric reflector. Light can enter the volumetric reflector, can propagate diffusely to various depths in the volumetric reflector, and can reflect from any of the depths in a diffuse (e.g., random) fashion. Using a volumetric reflector can increase an optical path length over which the gas sample can absorb light, which can be beneficial.

Figure 12:
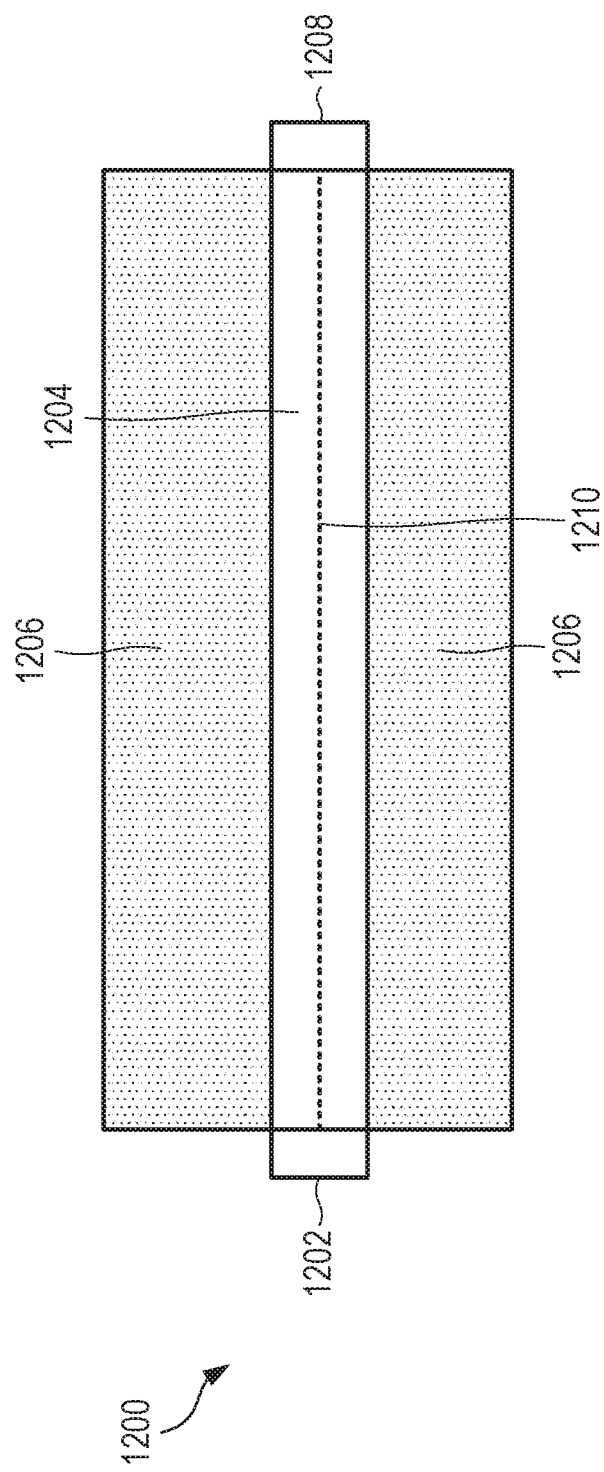
FIG. 12 shows a cross-sectional side view of an example of a gas sensing system having a volumetric reflector, in accordance with some embodiments.

FIG. 12 shows a cross-sectional side view of an example of a gas sensing system 1200 having a volumetric reflector, in accordance with some embodiments.

A light emitter 1202 can emit light into a gas chamber 1204 that is fillable with a gas sample. The gas chamber 1204 can be at least partially bound by a volumetric reflector 1206. At least some of the gas sample can permeate into the volumetric reflector 1206. The light from the light emitter 1202 can interact with the gas sample in a hollow portion of the gas chamber 1204 and with a portion of the gas sample that has permeated into the volumetric reflector 1206. A light sensor 1208 can receive the light from the gas chamber 1204. In some examples, the volumetric reflector 1206 can be shaped to define an elongated passage 1210 that extends from the light emitter 1202 to the light sensor 1208. Other shapes for the passage 1210 can be used. Other configurations can also be used.

In a specific example, the gas sensing system can include a cap. The cap can include three separate cavities that can be offset and fully divided. The cap can be located on a substrate. One or more emitters can be located on the substrate. One or more sensors can be located on the substrate. The one or more emitters can be located in one chamber, such as at a first longitudinal end of the cap. The one or more sensors can be located in another chamber, such as at a second longitudinal end of the cap. A middle chamber of the cap can include a cavity and can include a hole that can allow gas to enter the middle chamber of the cap. The middle chamber can function as a scattering, reflective, and/or resonant cavity. Light, such as infrared light, can travels through the sidewalls of the cap, can scatter around and interact with the gas inside, and can eventually be sensed at the sensor. The cavities above the emitter and detector can be metalized to improve light insertion into and/or extraction out of the cap. An exterior of the cap can be metallized to help retain light within the cap. The cap can be formed from a light-scattering ceramic material. The cap can be formed from a textured surface that is fully or at least partially reflective at the wavelength of the interaction with the sensed gas.

Figure 13:
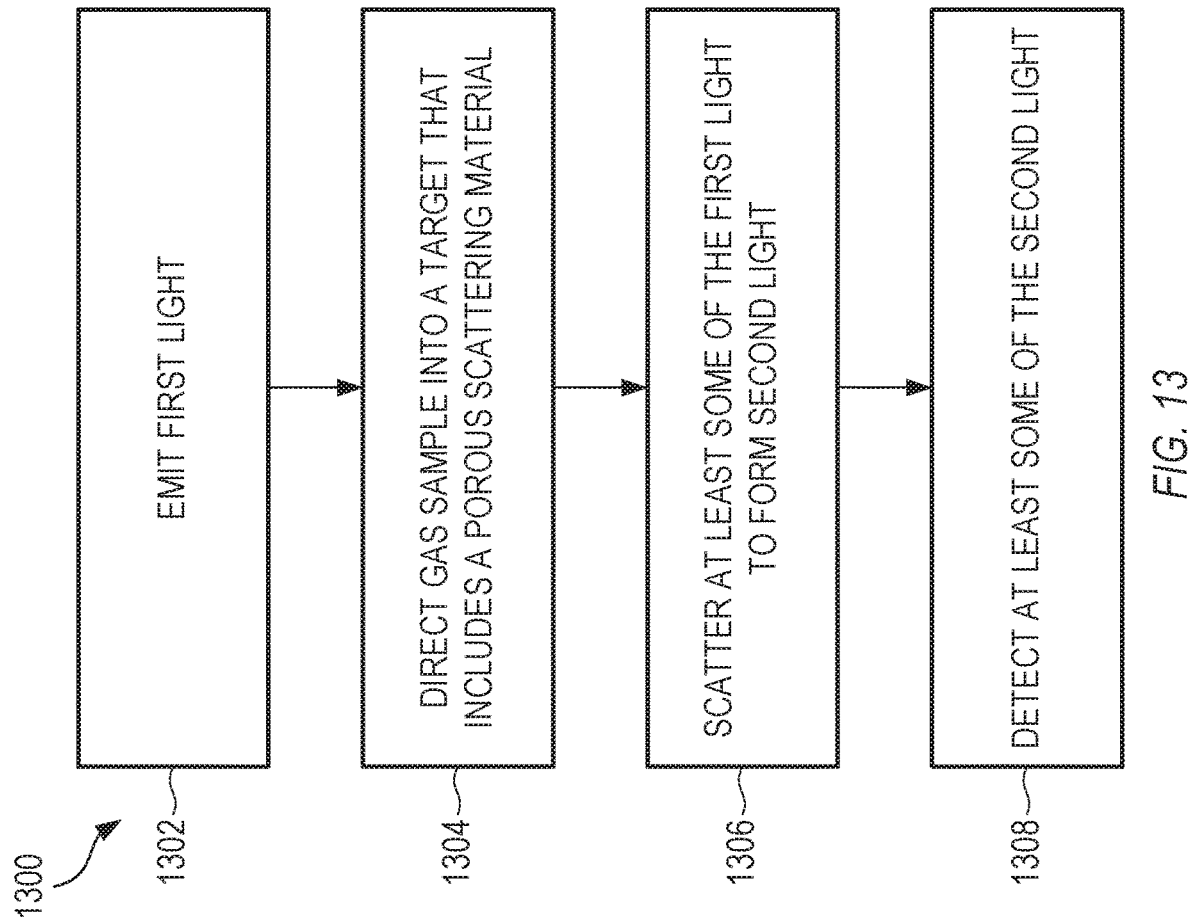
FIG. 13 shows a flow chart of an example of a method for measuring a concentration of a gas material in a gas sample, in accordance with some embodiments.

FIG. 13 shows a flow chart of an example of a method 1300 for measuring a concentration of a gas material in a gas sample, in accordance with some embodiments. The gas material can have an absorption peak at a first wavelength. The method can be executed on any of the gas sensing systems discussed herein, or on other suitable gas sensing systems.

At operation 1302, the method 1300 can include emitting first light having a spectrum that includes the first wavelength.

At operation 1304, the method 1300 can include directing the gas sample into a target. The target can include a porous scattering material that allows the gas sample to permeate within hollow spaces within the porous scattering material. The porous scattering material can be substantially transparent at the first wavelength.

At operation 1306, the method 1300 can include scattering, within the porous scattering material, at least some of the first light to form second light.

At operation 1308, the method 1300 can include detecting at least some of the second light.

While exemplary embodiments of the present disclosed subject matter have been shown and described herein, it will be obvious to those skilled in the art that such embodiments are provided by way of example only. Numerous variations, changes, and substitutions will now occur to those skilled in the art, upon reading and understanding the material provided herein, without departing from the disclosed subject matter. It should be understood that various alternatives to the embodiments of the disclosed subject matter described herein may be employed in practicing the various embodiments of the subject matter. It is intended that the following claims define the scope of the disclosed subject matter and that methods and structures within the scope of these claims and their equivalents be covered thereby.

What is claimed is:

1. A gas sensing system configured to measure a concentration of a gas material in a gas sample, the gas material having an absorption peak at a first wavelength, the gas sensing system comprising:
   an emitter configured to emit first light having a spectrum that includes the first wavelength;
   a target including a porous scattering material, the porous scattering material configured to allow the gas sample to permeate within hollow spaces within the porous scattering material, the porous scattering material being substantially transparent at the first wavelength, the porous scattering material configured to scatter at least some of the first light to form second light such that the second light emerges substantially isotropically from the target; and
   a sensor configured to detect at least some of the second light.

2. The gas sensing system of claim 1, further comprising at least one processor configured to determine a concentration of the gas material in the gas sample from a level of the second light at the sensor.

3. The gas sensing system of claim 2, wherein the at least one processor is further configured to determine the concentration from the Beer-Lambert Law.

4. The gas sensing system of claim 1, further comprising a wavelength filter located between the target and the sensor and configured to block at least one spectral portion of the second light having wavelengths away from the first wavelength.

5. The gas sensing system of claim 1, further comprising an emitter reflective package configured to reflect at least some of the first light toward the target.

6. The gas sensing system of claim 5, wherein the emitter reflective package defines a volume that is bounded by the target and a reflective inner surface of the emitter reflective package.

7. The gas sensing system of claim 1, further comprising a sensor reflective package configured to reflect at least some of the second light toward the sensor.

8. A The gas sensing system of claim 7, wherein the sensor reflective package defines a volume that is bounded by the target and a reflective inner surface of the sensor reflective package.

9. The gas sensing system of claim 1, further comprising a reflective package configured to reflect at least some of the first light toward the target and reflect at least some of the second light toward the sensor.

10. The gas sensing system of claim 9, wherein the reflective package defines a volume that is bounded by the target and a reflective inner surface of the reflective package.

11. The gas sensing system of claim 1, further comprising a reflector located at or near a surface of the target, the reflector configured to receive third light that has exited the target and reflect the third light to reenter the target.

12. The gas sensing system of claim 1, wherein the target is located between the emitter and the sensor.

13. The gas sensing system of claim 1, wherein the target is elongated along an axis that extends between a center of the emitter and a center of the sensor.

14. The gas sensing system of claim 1, wherein the target is elongated along a first axis that is substantially orthogonal to a second axis that extends between a center of the emitter and a center of the sensor.

15. The gas sensing system of claim 1, wherein:
the target is elongated along an elongation axis; and
the emitter and the sensor are located on a same side of a plane that includes the elongation axis.

16. A method for measuring a concentration of a gas material in a gas sample, the gas material having an absorption peak at a first wavelength, the method comprising:
emitting first light having a spectrum that includes the first wavelength;
directing the gas sample into a target, the target including a porous scattering material that allows the gas sample to permeate within hollow spaces within the porous scattering material, the porous scattering material being substantially transparent at the first wavelength;
scattering, within the porous scattering material, at least some of the first light to form second light such that the second light emerges substantially isotropically from the target; and
detecting at least some of the second light.

17. The method of claim 16, further comprising determining a concentration of the gas material in the gas sample from a level of the detected second light and from the Beer-Lambert Law.

* * * * *

UNITED STATES PATENT AND TRADEMARK OFFICE
CERTIFICATE OF CORRECTION

PATENT NO. : 12,019,017 B2  
APPLICATION NO. : 17/090090  
DATED : June 25, 2024  
INVENTOR(S) : Masui et al.

Page 1 of 1

It is certified that error appears in the above-identified patent and that said Letters Patent is hereby corrected as shown below:

In the Claims

In Column 13, Line 23, in Claim 8, delete "A The" and insert --The-- therefor

Signed and Sealed this  
Twenty-first Day of January, 2025

Coke Morgan Stewart  
*Acting Director of the United States Patent and Trademark Office*